Nov. 2, 1965 F. C. TOMLINSON Plant Pat. 2,567
FRAXINUS TREE
Filed Sept. 16, 1963
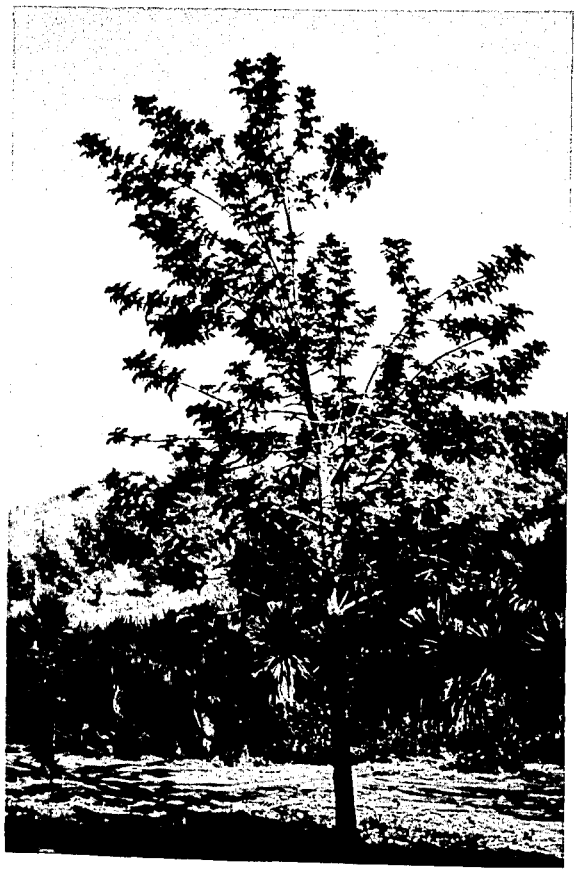
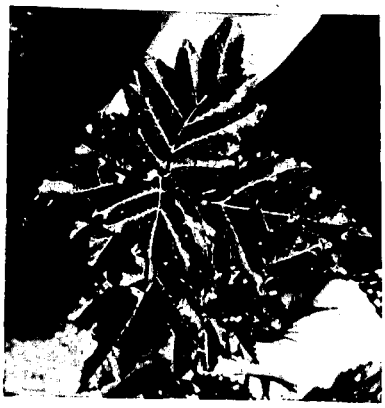
INVENTOR
FRANCIS C. TOMLINSON
BY J. F. Cuneo
ATTORNEY United States Patent Office Plant Pat. 2,567
Patented Nov. 2, 1965

2,567
FRAXINUS TREE

Francis C. Tomlinson, 524 N. Painter, Whittier, Calif.

Filed Sept. 16, 1963, Ser. No. 309,364
1 Claim. (Cl. Plt.—51)

This invention relates to a new and distinct variety of Fraxinus tree and particularly to an evergreen Fraxinus tree.

I discovered the new variety of Fraxinus tree in my growing grounds located at 11758 East Whittier Boulevard, Whittier, county of Los Angeles, State of California, in July of 1954. The new variety originated as a so-called chance seedling in a group of cultivated *Fraxinus uhdei,* the pollen parent is unknown.

The new variety has been asexually reproduced by me on my property in Whittier, California, primarily by grafting. A very large number of grafts of the new and distinct variety have been made since its discovery, and in all instances the descendants have exhibited the distinguishing characteristics of the new variety. The new variety cannot be reproduced true from seed, in fact the tree has never been observed to produce seed.

The new and distinct variety is characterized as to novelty by its smaller size and its very slow growth, its thick, coriaceous leaflets that have a serrated margin that is very undulate, by its husky stems supporting compound leaves that are odd-pinnate and by its very pronounced veins that are particularly heavy on the underside of the leaflet.

In comparison with the seed parent, *Fraxinus uhdei,* among which the new variety was discovered, the new variety exhibits the following distinguishing characteristics:

The new variety and all of its descendants reach a height of only fifteen feet and a spread of ten feet in nine years, whereas the *Fraxinus uhdei* plants grown under the same growing conditions reach a height of twenty-five feet and a spread of twenty feet in only three years, and these same trees will reach a height of from fifty to sixty feet and a spread of from fifty to sixty feet when they are only six years old.

The leaflets of the new variety are thick, coriaceous and have a serrate margin that is very undulate, greatly resembling the leaf of an ilex in this characteristic. The leaflets average three inches in length and are from one to two and one-quarter inches in width; occasionally some leaflets may reach a length of four inches, however, the number of these leaflets is rather small. The shape of the leaflets is substantially obtuse and the leaflets have a mucronulate tip with the base obtuse. The arrangement of the compound leaves is odd-pinnate and the leaflets are opposite. The distance between adjacent pairs of leaflets varies from five eighths of an inch to a maximum distance of one and one-half inches depending on the size and position of the pairs on the stem. The veins of the leaflets are prominent particularly on the underside of the leaflet.

The leaflets of the seed parent, *Fraxinus uhdei* are in contrast thin and smooth. Their margins have widely spaced serrations and are not undulate or "crinkly." These leaflets can attain a length up to five inches and a width of two and three-quarters inches at the widest portion of each leaflet. The leaflets are obovate with a substantially cuspidate tip and with the base attenuate. The veins are not very prominent and the leaflet pairs are widely separated on the stem with some pairs being two and one half inches apart.

The petioles of the new variety can be described as almost sessile with some of the petioles reaching almost one inch in length. The petiole of *Fraxinus uhdei* is generally three to four inches in length.

The leaflets of the new variety do not resemble the leaflets of *Fraxinus uhdei* at all, and botanical experts when first viewing the new variety have most frequently classed the plant as a photinia.

The stems supporting the compound leaves of the new variety are particularly husky, even on trees that are only six feet high. These stems range from one-half to five-eighths of an inch in thickness near their point of attachment, and are from one-quarter to five-sixteenths of an inch in thickness, even at the point from which the terminal compound leaf starts. The corresponding stems of *Fraxinus uhdei* in comparison are quite slender, being usually about three-sixteenths of an inch in thickness near the point of attachment, on an average, and tapering as they approach the point from which the terminal compound leaf starts, to from one-sixteenth of an inch to approximately one-eighth of an inch maximum.

The new variety has not produced any seed in nine years, whereas *Fraxinus uhdei* will produce seed in from four to five years.

The accompanying illustrations show in full color the entire tree as well as a terminal branch to better illustrate the thick, springy nature of the leaflets as well as their shape. These leaflets are a medium green and the colors in the photograph are as close as they could be reproduced by this method of illustration. To facilitate identification of the important colors the terminology adopted by the British Horticultural Colour Charts has been adopted.

A detailed description of the new and distinct variety follows:

*The tree*

Parentage: Chance seedling from a group of *Fraxinus uhdei*; pollen parent is unknown.

Growth: The tree has a vigorous, upright growth with ascending branches.

Height: The original tree was discovered in July of 1954, and since that time it has attained a height of about fifteen feet and has a spread at the widest portion of approximately ten feet. The tree tapers toward the top as is shown in the illustration.

Trunk: The trunk of the tree is approximately six inches in diameter and is covered with a smooth, light grey bark.

Branches: The branches of this new variety of ash are thick and husky and this feature is observed even at the terminal portions of the branches and stems; the thickness of the stems supporting the compound leaves being one-quarter to five-sixteenths of an inch at the point from which the terminal compound leaf attaches, and increasing to five-eighths inches at the point of attachment to the branch; this characteristic is attributed to the very slow growth of the tree.

Foliage:

*Texture.*—The leaflets are thick and coriaceous and are very springy, somewhat reminding one of a holly leaf.

*Shape.*—The leaflets are best described as obtuse when they are flattened out, with the base substantially obtuse and having a mucronulate to obtuse tip. The margins are serrate and the edge or outer portion of the leaflet is strongly undulate, as shown in the closeup view.

*Arrangement.*—Leaves are compound, odd-pinnate and opposite and each pair of leaflets is located from ⅝" to 1½" from the preceding pair.

*Size.*—Fully matured leaflets are on an average, three inches in length, and occasionally a leaflet may reach four inches in length. The leaflets can be from one and one quarter inches across the widest portion of the leaflet, up to 2¼" in width.

*Color.*—New growth: upper side—Parsley Green oo962, with a definite coppery red overtone; under side—Parsley Green oo962/1, also with a coppery red overtone. Mature growth: upper side—Parsley Green oo962/2; under side—Willow Green ooo862.

*Petioles.*—The petioles are usually quite short; the petiole varies from almost sessile to one inch in length.

*Petiolule.*—The petiolules are generally quite short, the longest petiolule does not exceed 3/16″ in length.

*Veins.*—The under side of each leaflet has thick prominent veins that continue without substantial reduction in width for the major portion of its length; the veins extend from a heavy midrib. The veins on the upper side of the leaflet are not quite so prominent but are nevertheless quite noticeable. The venation of the leaflets is best described as pinnate.

Having described my invention, I claim:

The new and distinct evergreen variety of Fraxinus tree substantially as shown and described, characterized particularly as to novelty by its crinkly, substantially obtuse leaflets having a mucronulate to obtuse tip with the base obtuse, that are thick, coriaceous and springy, by the serrate leaflet margin that is very undulate, by its ascending branches forming a tapering crown, by its relatively small size and slender trunk, by its thick husky stems that support the compound leaves, by the prominent, heavy veins that extend from a heavy midrib of the leaflets and by its slow growth.

No references cited.

ABRAHAM G. STONE, *Primary Examiner.*